United States Patent [19]

Wortham et al.

[11] Patent Number: 4,838,858
[45] Date of Patent: Jun. 13, 1989

[54] APPARATUS AND METHOD FOR ADMINISTERING FLUIDS

[75] Inventors: Samuel T. Wortham, Northport, N.Y.; Sidney Krakauer, Highland Beach, Fla.

[73] Assignee: Pall Corporation, Glen Cove, N.Y.

[21] Appl. No.: 838,478

[22] Filed: Mar. 11, 1986

[51] Int. Cl.⁴ ............................................. A61M 5/00
[52] U.S. Cl. ...................................... 604/83; 604/257
[58] Field of Search .............................. 604/80, 82–85, 604/280, 283, 284, 256, 257, 411, 905

[56] References Cited

U.S. PATENT DOCUMENTS

| | | | |
|---|---|---|---|
| 3,982,534 | 9/1976 | Buckman | 128/214 |
| 4,191,183 | 3/1980 | Mendelson | 128/214 |
| 4,236,515 | 12/1980 | Genese | 128/214 |
| 4,237,879 | 12/1980 | Genese | 128/214 |
| 4,430,074 | 2/1984 | Mooring | 604/49 |
| 4,512,764 | 4/1985 | Wunsch | 604/80 |
| 4,533,347 | 8/1985 | Deckert | 604/81 |
| 4,573,974 | 3/1986 | Ruschke | 604/81 |
| 4,661,110 | 4/1987 | Fortier et al. | 604/284 X |
| 4,734,091 | 3/1988 | Boyle et al. | 604/257 X |

*Primary Examiner*—Stephen C. Pellegrino
*Attorney, Agent, or Firm*—Leydig, Voit & Mayer

[57] ABSTRACT

The disclosure describes an administration set for providing a flow of fluid from a fluid container to a patient and comprising a section of tubing for channeling the fluid to the patient, an inlet spike attached to the tubing and connectable to the container for establishing a flow of fluid into the tubing, a connector attached to the tubing downstream from the inlet spike for sealingly receiving an inlet spike from a second administration set, and an arrangement operatively associated with the tubing and the connector for directing a flow of fluid into the inlet spike of the second administration set.

26 Claims, 2 Drawing Sheets

APPARATUS AND METHOD FOR ADMINISTERING FLUIDS

TECHNICAL FIELD

The present invention relates to an apparatus and method for intravenously administering fluids from one or more fluid containers to a patient.

DISCLOSURE OF THE INVENTION

Administration sets are typically used to administer fluids to a patient intravenously. Typically, an administration set includes a length of tubing for channeling the fluid from a container to the patient. A hollow inlet spike is mounted to one end of the tubing and inserted into the container while a needle is mounted to the opposite end of the tubing and inserted into the vein of a patient, establishing a flow of the fluid from the container through the tubing to the patient. The administration set may further include a drip chamber mounted in the tubing and one or more clamps for interrupting fluid flow through the tubing.

While conventional adminstration sets have proven very effective, they nonetheless have certain undesirable characteristics. For example, once the fluid container is empty, flow through the administration set stops and a residual amount of the fluid remains in the tubing. If the fluid is a therapeutic fluid, i.e., a fluid containing a drug or other medicinal solution, it should be in the patient rather than in the tubing. Further, if a second therapeutic fluid is to be administered to the patient but is not chemically or otherwise compatible with the residual therapeutic fluid remaining in the administration set, a second administration set will be required to administer the second therapeutic fluid. A patient who needs several different types of therapeutic fluids may then require several administration sets, increasing his medical costs.

In accordance with one aspect of the invention, an apparatus is provided for flushing a fluid, e.g., a therapeutic fluid, from an administration set. The apparatus comprises a section of tubing which channels a flow of a second fluid, e.g., a neutral maintenance fluid, and an arrangement mounted to the tubing section for receiving the inlet spike of the administration set and directing at least a portion of the flow of maintenance fluid through the administration set. In this manner, the residual therapeutic fluid contained in the administration set is flushed into the patient and the administration set is then available to administer a second therapeutic fluid.

In accordance with another aspect of the invention, an improved administration set is provided comprising a length of tubing for channeling a fluid, such as a maintenance fluid, to the patient and an inlet spike attached to the tubing and connectable to the maintenance fluid container for establishing a flow of the maintenance fluid into the tubing. The administration set also comprises a connector attached to the tubing downstream from the inlet spike and capable of receiving an inlet spike of a second administration set which may, for example, contain a residual amount of a therapeutic solution. The administration set according to the invention then further comprises a mechanism attached to the tubing and the connector for directing at least a portion of the flow of the maintenance fluid into the inlet spike of the second administration set. Again, the flow of the maintenance fluid through the second administration set flushes the residual therapeutic fluid into the patient.

In accordance with yet another aspect of the invention, a method is provided for flushing a fluid such as a therapeutic fluid from a first administration set. The first administration set includes a detachable connector mounted to a container of the therapeutic fluid. The method comprises the steps of detaching the connector of the first administration set from the container of the therapeutic fluid, attaching the connector to a second administration set channeling a flow of another fluid, e.g., a maintenance fluid, to the patient, and then directing at least a portion of the maintenance fluid flowing through the second administration set into the first administration set.

BEST MODE FOR CARRYING OUT THE INVENTION

Figure 1:
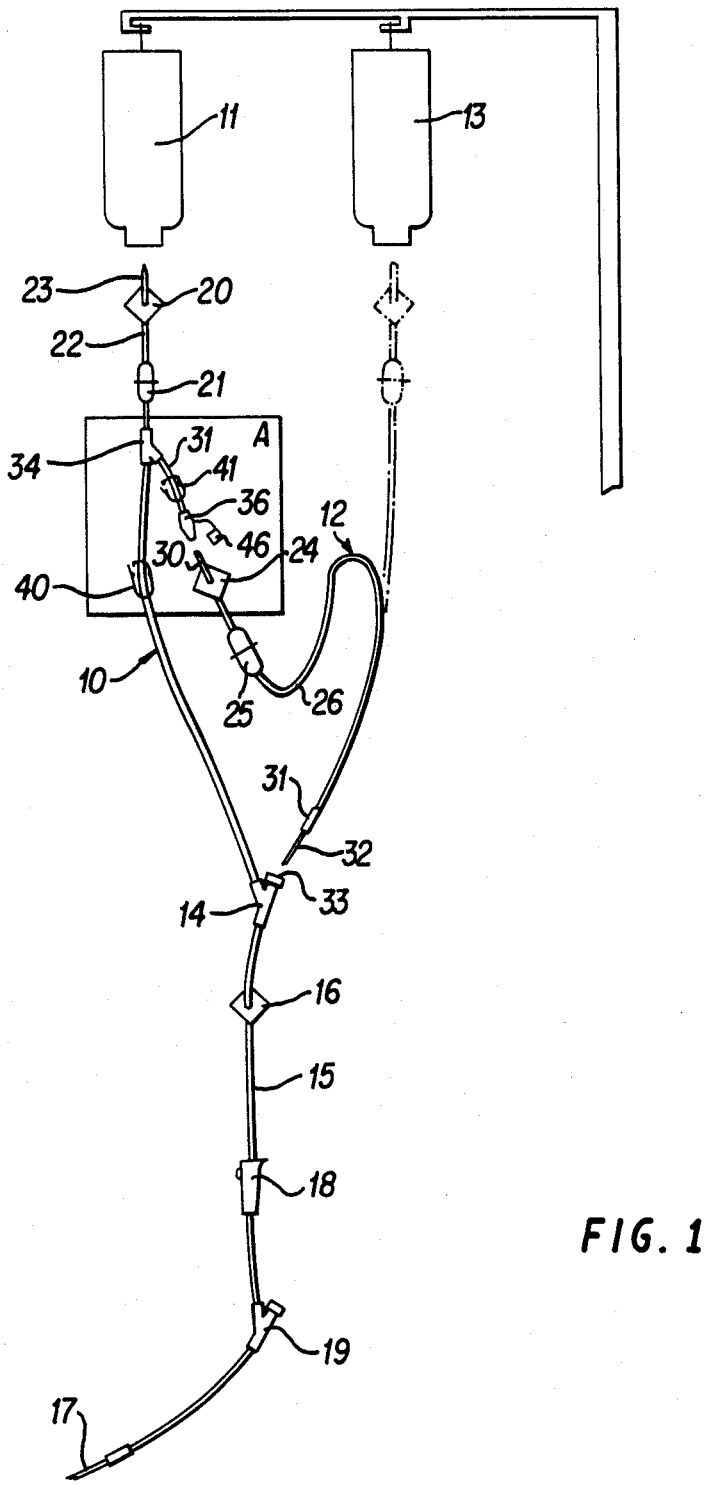
FIG. 1 is an elevation view of an exemplary administering system embodying the invention.

As shown in FIG. 1, an exemplary administering system constructed and operated in accordance with the invention generally comprises a primary administration set 10 for administering fluid from a first container 11 to a patient (not shown) and a second administration set 12 for administering fluid from a second container 13 to the patient. The primary and secondary adminstration sets 10, 12 may be independently attached to the patient. However, in the exemplary system, the first and second fluids flowing through the primary and secondary administration sets 10, 12, respectively, are combined by a junction element 14 and channeled by a common tube 15 through a filter 16 to the patient via a needle 17. The filter 16 downstream from the junction element 14 is especially preferable because it ensures that all fluids being administered to the patient through the primary and secondary administration sets 10, 12 have been filtered at least once. A flow regulator 18 and a second junction element 19, which may conveniently serve as an injection port, may also be mounted in the common tube 15.

The primary administration set 10 includes a filter 20 and a drip chamber 21 serially mounted in a tubing section 22 which is attached to the junction element 14. To establish a flow of the first fluid through the primary adminstration set 10, a rigid tubular inlet structure, such as the inlet spike end 23 of the filter 20, may be inserted into the first container 11. The filter 20, drip chamber 21 and tubing section 22 then cooperate to channel the first fluid to the common tube 15 where it is then channeled to the patient.

In the exemplary administering system, the drip chamber 20 may preferably be fashioned from a resiliently deformable material. Further, both the filter 20 in the tubing section 22 and the filter 16 in the common tube 15 are preferably designed to remove a variety of substances, including various emboli, bacteria and endotoxins, i.e., toxins produced as a result of bacterial growth or decomposition. By incorporating such filters, the useful lifetime of the administration system may be greatly extended, e.g., from a rating of 24 to 96 hours. Filters, such as those available from Pall Corporation under the trademark SCF or the trademark SET SAVER, should prove particularly suitable.

The secondary administration set 12, which is similar to the primary administration set 10, may preferably include an identical filter 24 and drip chamber 25 serially mounted in a tubing section 26. As shown by the dotted lines in FIG. 1, the inlet spike end 30 of the filter 24 may similarly be inserted into the second container to establish a flow of the second fluid into the secondary administration set 12. However, unlike the primary administration set 10, the secondary administration set 12 is joined to the junction element 14 by means of an adapter 31 which securely connects a needle 32 to the end of the tubing section 26. The junction element 14 has a rubber-stoppered end 33 into which the needle 32 may be inserted, allowing the second fluid to flow from the second container 13 to the patient.

Figure 2:
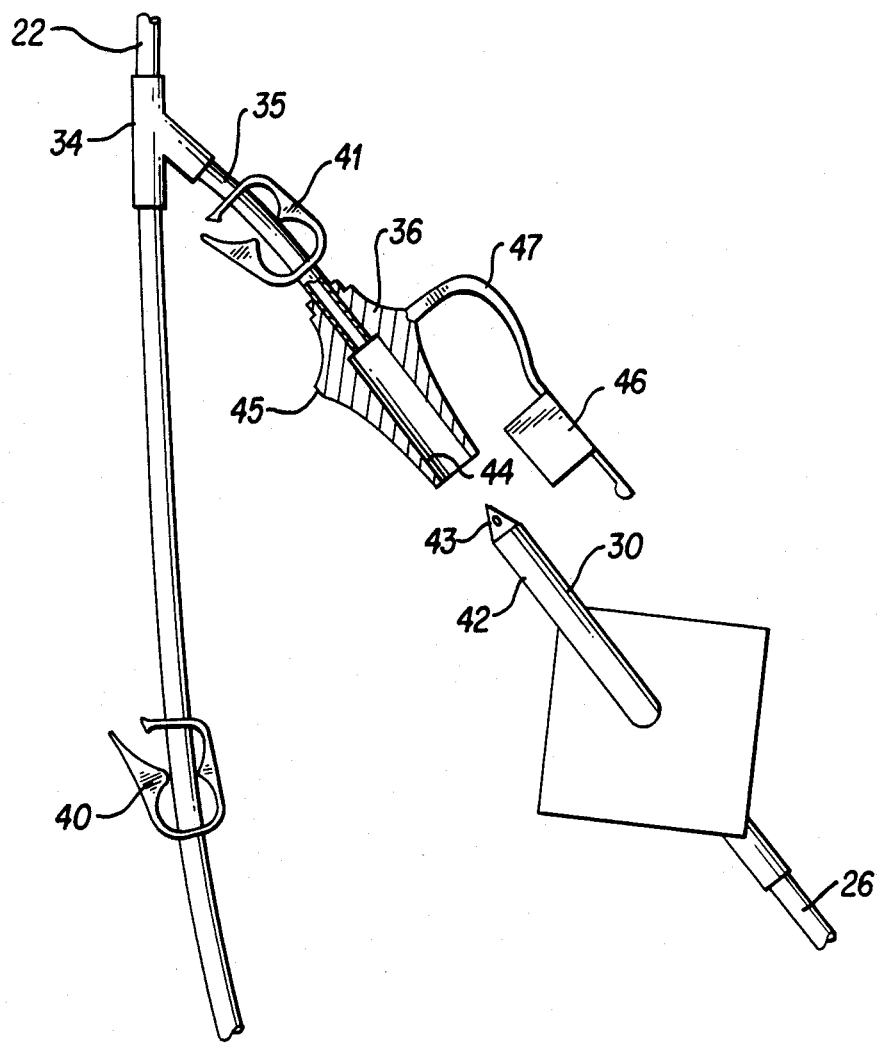
FIG. 2 is a partially sectional elevation view of the components shown in Rectangle A of FIG. 1.

In accordance with one aspect of the invention, the secondary administration set 12 may be connected to the primary administration set 10 and the flow of the first fluid through the primary administration set 10 may be directed at least partially through the secondary administration set 12. As shown in FIG. 2, a branching connector, such as a bifurcating element 34, is mounted in the tubing section 22 of the primary administration set 10 downstream from the filter 20 and the drip chamber 21. The bifurcating element 34 divides the flow of the first fluid into a first branch extending along the tubing section 22 to the junction element 14 and a second branch extending along a short interconnecting tube 35 to a connector 36. To selectively prevent the flow of the first fluid through the first and second branches and direct fluid through one branch or the other, a first clamp 40 is mounted to the tubing section 22 downstream from the bifurcating element 34 and a second clamp 41 is mounted to the interconnecting tube 35. Alternatively, other flow control devices, such as flow regulators, may be used instead of the clamps 40, 41.

The connector 36, which is preferably fashioned from a resilient material, is designed to couple with the rigid tubular inlet structure of the second administration set 12. Consequently, the connector 36 may be variously configured in accordance with the configuration of the inlet structure. For example, the rigid tubular inlet structure of the secondary administration set 12 comprises a spike end 30 of the filter 24. The spike end 30 is configured as a hollow cylinder 42 with a pointed open end 43. Preferably, the connector 36 then comprises a cylindrical wall structure 44 defining an inside diameter and length corresponding to those of the cylinder 42 of the spike end 30. The connector 36 may also include a flared portion 45 to facilitate grasping the connector and a removable cap 46 connected to the flared portion 45 via a flexible link 47. The removable cap 46 covers one end of the cylindrical wall structure 44 and maintains the sterility of the cylindrical wall structure 44 when the connector 36 is not in use.

Alternatively, the connector may be configured as a valve structure with an orifice portion that is normally biased closed to prevent flow of fluid through the second branch and maintain sterility within the orifice. The orifice portion may be forced open, however, by insertion of the rigid tubular inlet structure of a secondary administration set, allowing flow into the secondary administration set. With such a connector, the clamp 41 in the interconnecting tube 35 may be eliminated.

In the preferred mode of operation, both the primary and secondary administration sets 10, 12 may be connected between the patient and the first and second containers 11, 13, respectively. Thus, for example, the first container 11 may contain a maintenance fluid while the second container 13 may contain a therapeutic fluid. The patient then receives both the maintenance fluid and the therapeutic fluid in a "piggyback" manner via the primary and secondary adminstration sets 10, 12.

Once the second container 13 has been drained or a predetermined amount of the therapeutic fluid has been administered, it will frequently be desirable to flush the therapeutic fluid from the secondary administration set 12. In accordance with another aspect of the invention, an exemplary method for flushing the secondary administration set 12 comprises closing the second clamp 41 on the interconnecting tube 35 and removing the cap 6 from the connector 36. The inlet spike end 30 of the secondary administration set 12 is then removed from the second container 13 and inserted into the connector 36 on the primary administration set 10. The second clamp 41 on the interconnecting tube 35 is then opened and the first clamp 40 on the tubing section 22 is closed, directing the flow of the maintenance fluid from the first container 11 along the first administration set 10 to the bifurcating element 34 and through the second administration set 12 via the interconnecting tube 35 and connector 36. The cylindrical wall structure 44 of the connector 36 tightly engages the cylinder 42 of the inlet spike end 30, sealing one to the other and preventing leakage of the maintenance fluid.

After the therapeutic fluid has been flushed from the second administration set 12, the second clamp 41 can be closed and the first clamp reopened to re-establish flow of the maintenance fluid along the primary administration set 10. The secondary administration set 12 may conveniently remain connected to the primary administration set 10 with the inlet spike end 30 of the secondary administration set 12 maintained in the sterile confines of the connector 36. In this manner, the inlet spike end 30 of the secondary administration set 12 is safely stored in a sterile environment until it is again necessary to administer another therapeutic fluid.

To administer the subsequent therapeutic fluid, the inlet spike end 30 of the secondary administration set 12 may be removed from the connector 36 and attached to another container while the cap 46 is replaced on the end of the connector 36. The maintenance fluid and the therapeutic fluid are then again administered to the patient in a piggyback fashion via the primary and secondary administration sets 10, 12. Although the present invention has been described in terms of a particular embodiment, it is not limited to this embodiment. Alternative embodiments and modifications which would still be encompassed by the invention may be made by those skilled in the art, particularly in light of the foregoing teachings. Therefore, the following claims are intended to cover any alternative embodiments, modifications or equivalents which may be included within the spirit and scope of the invention.

We claim:

1. An apparatus for flushing an administration set which channels a flow of a first fluid to a patient and which includes a detachable connector mountable to a container of the first fluid, said apparatus comprising tubing means for channeling a flow of a second fluid and means connected to the tubing means for receiving the detachable connector of the administration set and directing at least a portion of the flow of the second fluid through the administration set.

2. The apparatus of claim 1 wherein the receiving and directing means includes means connected to the tubing means for dividing the flow of the second fluid into at least first and second branches and connector means mounted in the second branch for sealingly receiving the detachable connector.

3. The apparatus of claim 2 wherein the dividing means comprises a bifurcating element.

4. The apparatus of claim 2 wherein the connector means comprises means for sealingly engaging a spike.

5. The apparatus of claim 2 wherein the connector means comprises a hollow connector having first and second ends, a cylindrical wall means extending between the first and second ends for engaging the detachable connector of the administration set, and a cap removably connected to the first end of the hollow connector.

6. The apparatus of claim 5 wherein the receiving and directing means further includes a flexible tubular portion connected to the second end of the hollow connector and extending between the hollow connector and the dividing means.

7. The apparatus of claim 6 wherein the receiving and directing means includes means attached to the tubular portion for selectively controlling fluid flow through the tubular portion.

8. The apparatus of claim 7 wherein the receiving end directing means further includes means operatively associated with the first branch for selectively controlling fluid flow through the first branch.

9. The apparatus of claim 8 wherein each flow controling means comprises a clamp.

10. An adminstration set for providing a flow of fluid from a fluid container to a patient, said administration set comprising:
    tubing means for channeling fluid to the patient;
    spike means attached to the tubing means and connectable to the container for establishing a flow of fluid into the tubing means;
    connector means attached, to the tubing means downstream from the spike means for sealingly receiving a spike means from a second administration set; and
    means operatively associated with the tubing means and the connector means for directing a flow of fluid into the spike means of the second administration set.

11. The administration set of claim 10 wherein the directing means comprises a branching element connected to the tubing means and a tubular portion mounted to the branching element and wherein the connector means comprises a connector mounted to the tubular portion and having a cylindrical wall means for engaging the spike inlet means of the second administration set and cap means removably mounted to the connector for preventing fluid flow.

12. The administration set of claim 11 wherein the directing means further includes clamp means mounted to the tubular portion for controling fluid flow through the tubular portion.

13. The administration set of claim 12 further comprising clamp means mounted to the tubing means downstream from the connector means for controlling fluid flow through the tubing means.

14. The administration set of claim 13 wherein the tubing means includes a drip chamber disposed upstream from the connector means.

15. The administration set of claim 14 wherein the tubing means further includes junction means disposed downstream from the connector means for sealingly receiving an outlet means of the second administration set.

16. A method for flushing a first fluid from a first administration set which channels a flow of the first fluid to a patient and which includes a detachable connector mounted to a container of the first fluid, said flushing method comprising the steps of detaching the connector of the first administration set from the container; attaching the connector of the first administration set to a second administration set channeling a flow of a second fluid to the patient; and directing at least a portion of the second fluid flowing through the second administration set into the first administration set.

17. The flushing method of claim 16 wherein attaching the connector includes connecting a rigid tubular inlet structure to a hollow receiving member.

18. The flushing method of claim 17 wherein connecting the rigid tubular inlet structure includes inserting an inlet spike of the first administration set into a cylindrical wall means of the second administration set.

19. The flushing method of claim 16 wherein directing the second fluid into the first administration set includes dividing the flow of the second fluid through the second administration set into first and second portions, channeling the first flow portion into the first administration set, and clamping the second flow portion.

20. An administration set which administers first and second fluids respectively contained in first and second containers, the administration set comprising:
    a first spike insertable into the first container;
    a first tubing arrangement connected to the first spike;
    a second spike insertable into the second container;
    a second tubing arrangement connected to the second spike; and
    a structure mounted to the first tubing arrangement for receiving the second spike and channeling at least a portion of the first fluid into the second spike.

21. The administration set of claim 20 further comprising a junction element joining the first and second tubing arrangements and a third tubing arrangement connected between the junction element and a patient.

22. The administration set of claim 20 wherein each spike includes a filter having an inlet spike end and wherein each tubing arrangement includes a drip chamber disposed downstream from the filter.

23. An administration set comprising:
    a spike mountable to a first container of fluid;
    a tubing arrangement connected to the spike, the tubing arrangement including a branching element dividing the tubing arrangement into first and second branches; and
    a connector mounted in the second branch of the tubing arrangement and including a structure for receiving a spike mountable to a second container of fluid.

24. The administration set of claim 23 wherein the tubing arrangement further includes a drip chamber disposed between the branching element and the spike mountable to the first container of fluid.

25. The administration set of claim 23 wherein the spike includes a filter having an inlet spike end.

26. The administration set of claim 23 wherein the tubing arrangement includes a drip chamber disposed between the spike and the branching element.

* * * * *